United States Patent [19]

Byer

[11] Patent Number: 5,387,952

[45] Date of Patent: Feb. 7, 1995

[54] FEEDBACK APPARATUS FOR SENSING HEAD POSITION

[76] Inventor: Harold Byer, 2901 Honey Run Rd., Ambler, Pa. 19002

[21] Appl. No.: 189,358

[22] Filed: Jan. 31, 1994

[51] Int. Cl.$^6$ .............................................. A61B 3/14
[52] U.S. Cl. ..................................... 351/208; 340/573
[58] Field of Search ............... 351/200, 205, 206, 208, 351/221; 128/645, 664, 665, 745; 340/686, 689, 573–575, 825.19; 341/21

[56] References Cited

U.S. PATENT DOCUMENTS

| | | | |
|---|---|---|---|
| 2,063,015 | 12/1936 | Ames, Jr. | 88/20 |
| 2,235,319 | 3/1941 | Jobe | 88/20 |
| 2,267,103 | 12/1941 | Ireland | 155/177 |
| 2,852,975 | 9/1958 | Radde | 88/1 |
| 3,614,763 | 10/1971 | Yannuzzi | 340/573 |
| 3,622,233 | 11/1971 | Blood et al. | 351/38 |
| 3,706,304 | 12/1972 | Sisler | 128/2 T |
| 3,777,738 | 12/1973 | Sugita et al. | 128/2 T |
| 3,904,280 | 9/1975 | Tate, Jr. | 351/1 |
| 3,969,020 | 7/1976 | Lynn et al. | 351/17 |
| 4,105,302 | 8/1978 | Tate, Jr. | 351/7 |
| 4,255,022 | 3/1981 | Kuether et al. | 351/226 |
| 4,357,079 | 11/1982 | Karasawa | 351/208 |
| 4,444,476 | 4/1984 | Simon et al. | 351/211 |
| 4,453,808 | 6/1984 | Takahashi et al. | 351/208 |
| 4,468,104 | 8/1984 | Nunokawa | 351/206 |
| 4,818,097 | 4/1989 | Linde | 351/203 |
| 4,874,236 | 10/1989 | Abraham | 351/205 |
| 5,035,500 | 7/1991 | Rorabaugh et al. | 351/226 |

*Primary Examiner*—William L. Sikes
*Assistant Examiner*—Huy Mai
*Attorney, Agent, or Firm*—Eckert Seamans Cherin & Mellott

[57] ABSTRACT

A feedback apparatus for physical examinations, particularly for optical devices used to examine the eyes, provides an examinee with a signal that tells the examinee whether or not he or she is maintaining the proper examination position. A headrest has a pressure or proximity sensitive sensor for enabling and disabling an annunciator producing a signal such as light or sound. In an optical viewer, the signal can be provided by controlled operation of a point light source on which the examinee is expected to focus. The switch can be a membrane switch mounted on a forehead stop. The examinee can perceive whether his or her head is positioned in the proper examination position. Moreover, when used as a fixation point, the examinee's attention remains fixed on the annunciation signal. The examinee (patient) need not be reminded by the physician to move back into place if the examinee inadvertently withdraws from positive pressure against the headrest.

18 Claims, 4 Drawing Sheets

FEEDBACK APPARATUS FOR SENSING HEAD POSITION

BACKGROUND OF THE INVENTION

1. Field of the Invention

The invention relates to the field of methods and apparatus for effecting physical examinations. In particular, the invention provides a sensing and feedback device responsive to the position of a patient relative to a nominal examination location, such that the patient is signalled to return to the correct examination location if he or she inadvertently moves away. Preferably, the device is provided in a head support for optical examinations and similar situations that require a relatively accurate and immobile head position, for example for focusing viewing apparatus on the patient's eye.

2. Prior Art

Various physical examinations of patients are common in the medical field for diagnosis, measurement, sensory testing, treatment and the like, and often require the physician to examine a particular area of the patient using a viewer or similar device. An eye examination is a good example that is fairly representative of the field of physical examination. For an eye examination using an optical viewer directed at the patient's eye, a particular relative position must be maintained between the patient's head and the viewing device, such that the viewing device is correctly aimed and focused at the proper focal length needed to view the tissues of interest. Similarly, if the patient is expected to view through a lens configuration or the like, a predetermined position of the patient's head relative to the lens configuration is required.

Ophthalmologists and the like often are equipped with examination devices having a number of alternative devices for viewing, testing and the like. Typically, the patient sits in a chair. A head rest is often provided, on which the patient rests his or her head during the examination. For obtaining a nominal head position, a chin rest and/or forehead rest define reference abutments. For maintaining the nominal position, it is typically the patient's duty to hold his or her head against these abutments. For variations among patients and for effecting different types of tests, the physician has various adjustments for aiming and focus. However, it is undesirable, inconvenient and time consuming for the physician to alter such adjustments during the examination. It is most advantageous if the patient can hold still, with the head comfortably engaged against the chin and/or forehead rests.

Common practice is simply to ask the patient to place his or her head in the proper examination position against the head rest, and to relax and hold still. Whereas typical headrests simply comprise a chin cup and a forehead-stop, the patient has some freedom to move his or her head in the headrest, particularly to the rear. To immobilize his or her head, the examinee (patient) must vigilantly maintain his or her head in the examination position; however, over the course of the examination patients frequently relax and move away from the nominal position, especially retreating from the forehead stop.

Of course the patient can feel the forehead stop and should be aware of his or her head position. Nevertheless, patients very frequently and apparently unknowingly or involuntarily shift away from the examination position. The physician then must ask the patient to move up against the headrest, or must refocus or re-aim the viewing apparatus as necessary. This occurs over and over during the physician's day of examinations, and is a major inconvenience and time waster that unfortunately results from human nature. Despite the best intentions, even the most diligent patient's attention, and his or her head, sometimes wander from correct position on the headrest.

Physicians who conduct eye examinations and the like find themselves perpetually cajoling the patients to resume the examination position. This situation is frustrating to the physician and may be embarrassing to the patient, who generally has the best intentions and is simply inattentive. Alternatives such as placing a strap around the back of the patient's head are unduly intrusive or uncomfortable. It would be desirable to relieve the physician of the role of reminding the patient to remain against the headrest, in a manner that is not unduly burdensome to the patient, and is reasonably polite.

SUMMARY OF THE INVENTION

It is an object of the invention automatically to sense a position of a patient during an examination or treatment, and to provide a signal perceptible to the examinee whenever the examinee is sensed to have become displaced from a nominal examination position.

It is another object of the invention to relieve the examiner of the responsibility of policing the examinee over whether the examinee is maintaining his or her head is in the proper examination position.

It is also an object of the invention to save time in the conduct of examinations such as eye examinations using viewing apparatus to view the patient.

It is a further object of the invention to remind an inattentive examinee to maintain his or her head in the proper examination position during an eye examination or the like, in an interactive manner.

It is still another object of the invention to integrate a sensing and feedback apparatus with an examination device such as an optical viewer.

These and other objects are accomplished by a feedback apparatus for physical examinations requiring an examinee to hold his or her head relatively immobile at an examination position, preferably the physical examination of an eye, comprising a sensor that detects head position and at least one of an optical, auditory or tactile signalling device responsive to the sensor, producing a signal that is perceptible to the patient, for reminding the patient automatically to return to a nominally correct position.

The examination apparatus generally comprises a headrest, an annunciator device perceptible to the patient, a sensor on the headrest responsive to the patient and including switching means, and a power source coupled to the annunciator device through the switching means. The headrest preferably comprises a frame that can be fixed in position relative to a viewer or the like. A chin-cup is attached to the frame for supporting the examinee's chin and a forehead stop abuts against the examinee's forehead. The chin-cup and forehead stop are spaced appropriately and can be adjustable in position.

In one embodiment, the sensor comprises a simple normally closed switch mounted on the forehead stop or between the forehead stop and the frame, spring biased to open or close a connection between the power source and the annunciator device when the patient's head is resting or not resting against the forehead stop. The switch is actuated by pressure from the examinee's forehead relative to the frame, and preferably is actuated by minimal pressure. The switch has at least two operative conditions respectively indicating that the patient's head is disposed in or out of the correct position, and can have one or more additional states, for example responsive to levels of pressure against the frame.

As an alternative to a spring biased switch, other proximity sensing devices are possible. For example, a capacitive or inductive sensor can be provided in or in association with the head rest for sensing the patient's head, or an optical path can be made or broken between a source and sensor as a function of head position, for operating the switching means.

According to one embodiment, the annunciator device comprises a lamp or LED light source that is visible to the patient, either in the field of direct view or peripherally. The light source can be a point light source that is activated when the patient is in position, and can be arranged by positioning or by lenses, half-silvered mirrors or other optical means to define a point in the field of view at which the patient is expected to focus. The patient must maintain correct position for the light source to remain illuminated, which arrangement is advantageous in that the patient's attention remains directed to the light source, and coincidentally to maintaining correct head position.

The signalling can also be auditory or can be by tactile pressure or vibration. For example, the power source can comprise an alternating current signal generator coupled through the switching means to an electromagnetic device such as a speaker or solenoid, or enabled and disabled as a function of the switching means, for producing a signal perceptible to the examinee.

The annunciator device can be operated in either a positive or negative sense. That is, the annunciator device can be powered when the head is in position and disabled when not in position, or vice versa. In any event, the signal changes status in response to a change in condition of the switching means. Accordingly, the examinee can perceive by automatic means whether his or her head is in the proper examination position or not.

There are a number of particular configurations for the sensor, switching means, power source and annunciator or signal generator that are particularly appropriate in connection with certain types of diagnostic equipment that are conventionally used for different types of physical examinations. For example, in a slit-lamp for an eye examination, the nominal examination position is such that the examinee faces directly into a lens of an examining scope of the slit-lamp. For a slit-lamp, an advantageous annunciator comprises a pair of laterally spaced lights disposed on opposite sides of the lens of the examining scope. The lights preferably are illuminated in response to the patient arriving at the nominal position against the head rest, causing the switching means to change state to power the lights. During examination by the slit-lamp, a relatively bright beam is trained on one or the other of the examinee's eyes, thereby making it difficult for the examinee to see the lights using that eye. However, the examinee's other eye can perceive the other light in the pair. Typically, the examinee's eyes move together when focusing on one of the lights. Therefore, by focusing the unilluminated eye on the respective light, the illuminated eye becomes fixed at a proper position as a result of the unilluminated eye fixing on the signal light.

The invention is particularly useful in a keratotometer. The keratotometer has an examining scope having a lens, and the examinee holds his or her head in a preferred examination position in which he or she stares directly into the lens. For examination by a keratotometer, the patient looks along a central optical axis of the examining scope. A preferred light source in that case provides a point of light, such as from an LED, arranged in position or displayed by optical means to the patient along this central optical axis.

A number of further alternatives will be apparent in connection with the following discussion of particular embodiments and examples of practical embodiments of the invention.

BRIEF DESCRIPTION OF THE DRAWINGS

There are shown in the drawings certain exemplary ;embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

Figure 1:
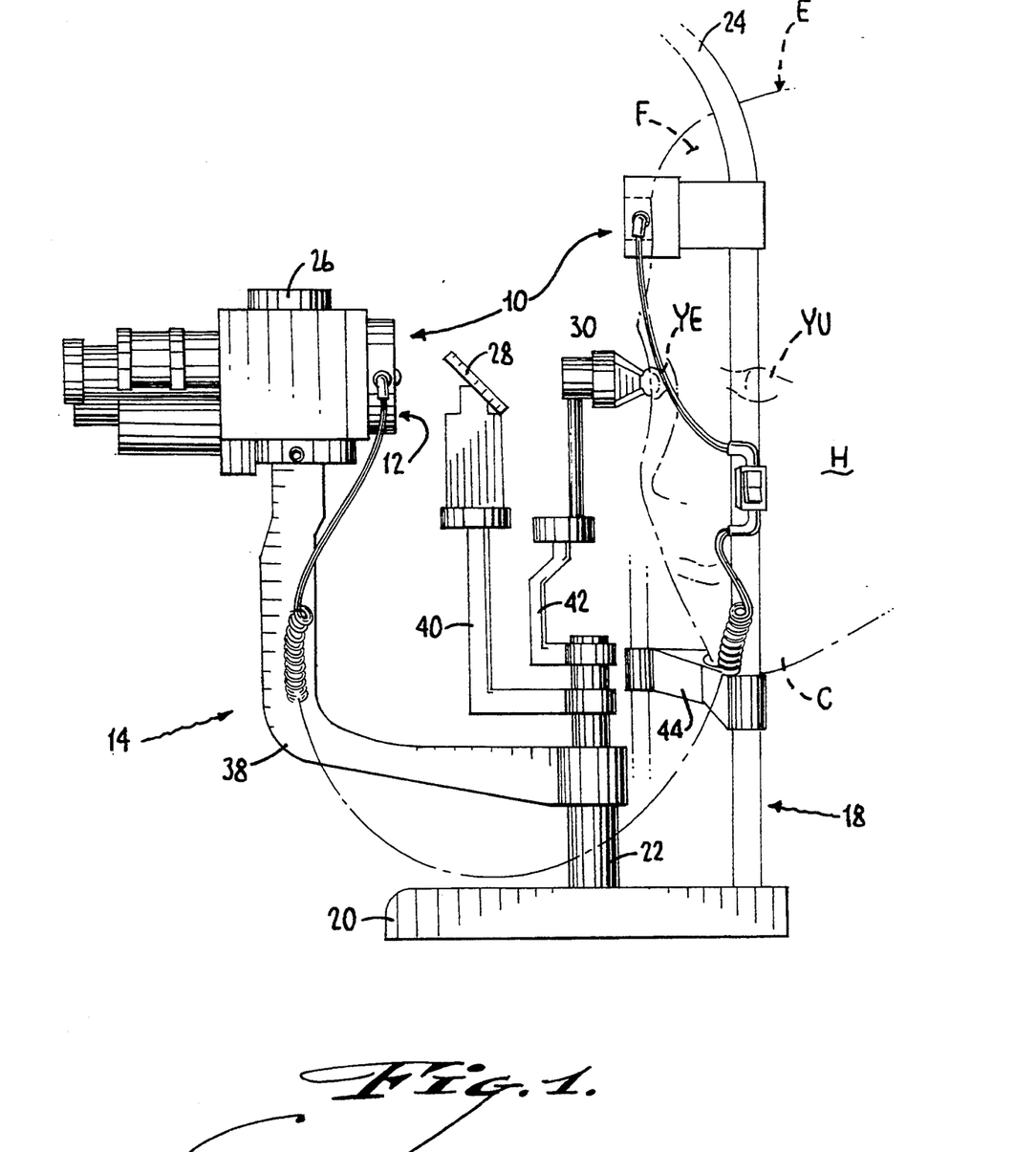
FIG. 1 is a side elevational view of a feedback apparatus according to the invention, for signalling the status of an examinee's head position, in this case shown between a forehead stop and a slit-lamp.

In FIG. 1, a feedback apparatus 10 according to the invention comprises an annunciator disposed between a lens 12 of a slit-lamp 14 and a forehead stop 16 of a headrest 18. The slit-lamp 14 is a well-known type of diagnostic equipment for eye examinations. The slit-lamp 14 comprises a base 20 supporting a mounting post 22 and an inverted-U bow 24 of the headrest 18. The mounting post 22 rotatably supports an examining scope 26 operated by the examining physician, a slit-type light source operating in conjunction with a reflector 28, and a diagnostic configuration or scope 30. Each of examining scope 26, slit-type light source 28, and diagnostic scope 30 are linked to the mounting post by L-shaped arms 38, 40 and 42, respectively, whereby they can be deployed or moved aside. More details on the typical components, operations, and uses of a slit-lamp are disclosed, for example, in U.S. Pat. Nos. 2,235,319 Jobe and 3,706,304 Sisler, which are incorporated herein by this reference.

The inverted-U bow 24 of the headrest 18 supports a chin-cup 44 and forehead stop 16 of head rest 18 relative to base 20, which commonly supports the illumination and viewing device(s) 26, 28, 30. An examinee E places his or her head H in headrest 18 in order to assume the correct examination position for the slit-lamp 14. More particularly, examinee E places his or her chin C in chin-cup 44, and presses his or her forehead F against forehead stop 16. The chin-cup 44 and forehead stop 16 cooperatively provide lateral, longitudinal and vertical opposition to mild pressure from examinee E to define and stabilize the examinee's head H at the proper examination position (generally as shown).

Figure 2:
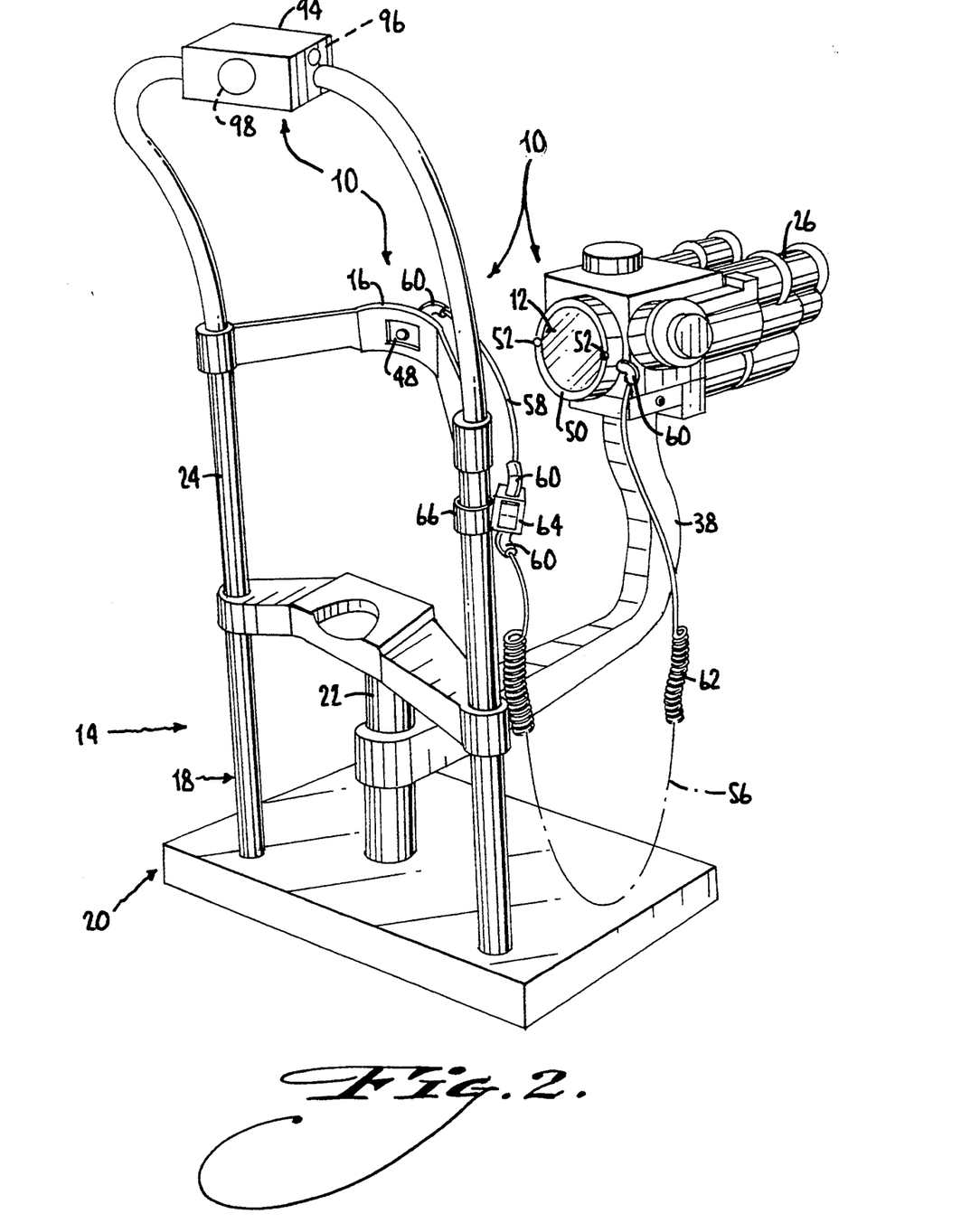
FIG. 2 is a perspective view further illustrating the apparatus according to FIG. 1.

In FIGS. 1 and 2, the feedback apparatus 10 comprises a sensor comprising a switch 48 mounted on the forehead stop 16. The annunciator comprises a split-ring 50 removably mounted on the lens 12 of the examining scope 26, carrying a pair of oppositely spaced LEDs 52. Electrical connection between the switching means of the sensor and the LEDs on split-ring 50 is made via a line cord 56 extending between the switch 48 and the split-ring 50. Line cord preferably includes phone jacks or the like for plugging the respective components together, or the line cord can be directly wired.

Switch 48 is actuated by pressure, preferably by minimal pressure from the examinee's forehead F while in the proper examination position. Accordingly, switch 48 is biased against pressure from the examinee. Such bias can be achieved in various ways, for example via the use of a pressure sensitive limit switch comprising a spring, an membrane type switch or the like. Alternatively, the forehead stop can be movable and spring biased to permit a slight displacement toward and away from the patient. In that case, the sensor and switching means can be mounted between the forehead stop and the frame to sense forehead pressure against the forehead stop.

According to this embodiment, the two LEDs 52 are spaced on the split-ring 50 at 180° apart and are mounted directly on the front face of the bezel such that the patient can focus on either one. The split-ring 50 is oriented on the lens 12 of the examining scope 26 such that the LEDs 52 lie in a same horizontal plane as the patient's eye, and the chin and forehead stops and/or the viewing device can be relatively adjusted vertically and horizontally as necessary to align the device and the patient's eyes. The arrangement shown has the horizontal plane that contains the LEDs 52 bisecting the lens 12 in equal upper and lower halves.

Preferably, the LEDs 52 are of different colors, such as one of the LEDs 52 being red while the other is green. This allows the examiner (who is not shown) to identify by color a specific one of the LEDs 52 on which the patient is expected to focus, which is more specific and helpful than by reference to the "left" or "right" LED, particularly since the patient can only see out of one eye when the other eye is illuminated.

The line cord 56 can include a flexible segment 58 extending between opposite plug-in connectors 60, that permits repositioning of the forehead stop on the frame, an extendible pigtail segment 62 between similar opposite plug-in type connectors 60 for rendering the connection compact while permitting movement of the viewer 26 on arm 38, and a battery case 64. A bracket 66 fixed to the inverted-U bow 24 holds the battery case 64 in a stable position on the frame. The flexible segment 58 is connected between the switch 48 and the battery case 64. The pigtail segment 62 is connected between the split-ring 50 and the battery case 64.

The examinee E places his or her head H in the headrest 18, with his or her chin C in the chin-cup 44 and forehead F against the forehead stop 16. As a result, the examinee E actuates the switch 48 against resilient bias. Switch 48 has at least two operative conditions. Switch 48 has a first condition corresponding to an object pressing against the forehead stop 16 and thereby actuating the switch 48. Additionally, the switch 48 has a second condition, corresponding to the object disengaging the forehead stop 16 and releasing the switch. In a preferred embodiment switch 48 is normally open, such that the LEDs are coupled by switch 48 to power from the battery when the patient is in position against the headrest. However, it would also be possible to operate the switch in the opposite sense. Switch 48 and the associated circuit can be configured either to couple or generate power or pulses to the LEDs upon actuation, or to make and break circuits corresponding to actuation and deactuation. A number of specific configurations are possible and should be apparent in view of the examples shown.

The LEDs 52 provide a patient perceptible annunciation signal which, in this case, is visible light. Although not effective to define a point of focus for the patient, other forms of annunciation are also possible. For example in an embodiment comprising an oscillator (not shown), the switching means can couple an AC signal to a speaker to produce a tone. Other electromagnetic means such as a solenoid (also not shown) can be provided to annunciate in the manner of a tactile signal applied to the patient. Any of these alternatives automatically remind the patient to remain engaged against the switch or other sensor.

LEDs 52 are preferred for their operation not only as indicator lights, but also as fixation lights or points of focus. During examination by the slit-lamp 14, a bright beam radiating from the slit-type light source 28 is trained on one or other of the examinee's eyes Y, which can be considered the examined eye YE. While the bright beam is trained thereon, the examinee E is temporarily more or less blinded in the examined eye YE. Still, the examinee E can tell whether the LEDs 52 are ON or OFF because such an indication is visible to the examinee E via his or her other eye YU. During this process, the patient can be asked by the physician to focus on the LED 52 on either side; however typically the patient is asked to focus on the LED 52 on the same side as the unexamined other eye YU. Whereas the patient's two eyes normally look in a same direction (apart from parallax when viewing close objects), this arrangement of LEDs 52 causes the examinee's examined eye YE to remain stable as long as the examinee's unexamined eye YU is fixed on one of the LEDs 52.

Figure 3:
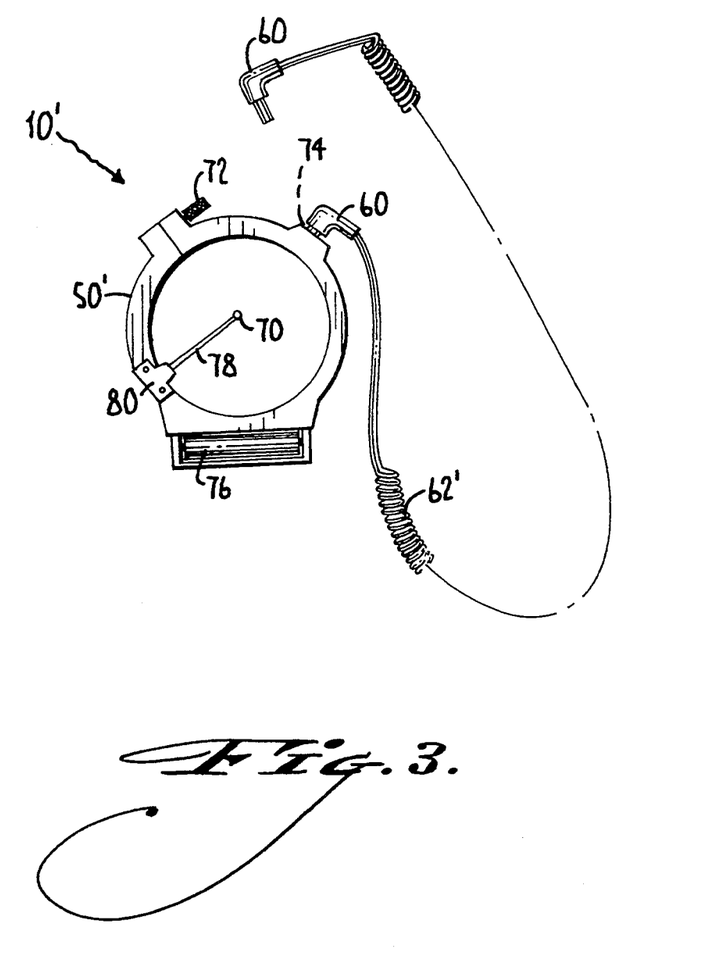
FIG. 3 is an elevation view of the annunciator portion according to an alternative embodiment of the invention, as seen substantially along a line viewed by a patient; and, FIG. 4 is a reduced-scale perspective view of the annunciator of FIG. 3, shown between a forehead stop and a keratotometer.

In FIG. 3, an embodiment 10' of the annunciator portion of a preferred feedback apparatus comprises a split-ring 50', a pigtail line cord 62', and an LED 70. The split-ring 50' includes a thumb screw 72 for securing the split-ring =' on the front of the scope of an eye examination instrument. The split-ring =' includes a socket 74 and a battery compartment 76. The split-ring =' carries a bracket 78 which extends from a base 80 attached to the split-ring =' to a distal end carrying the LED 70. The LED 70 is positioned on the central axis of the circular opening defined by the split-ring ='. The pigtail line cord 62' extends between opposite plug-in type connectors 60, one connector 60 being coupled to the socket 74 in the split-ring ='.

Figure 4:
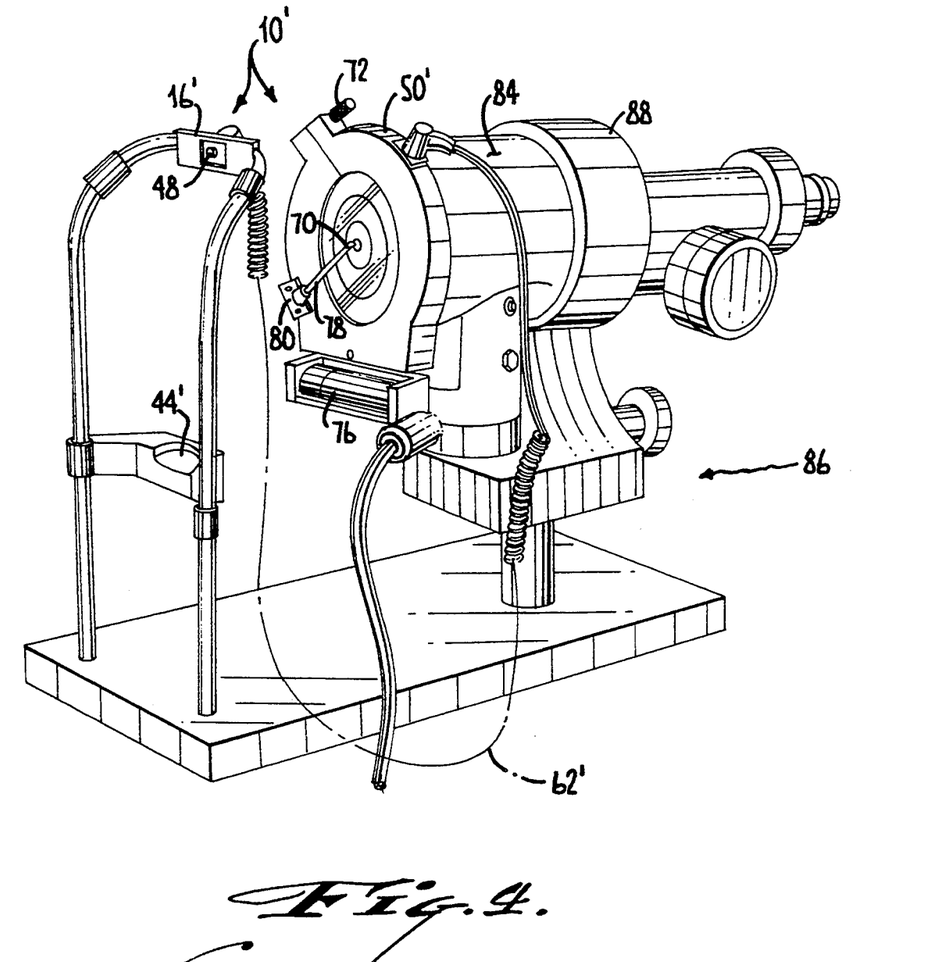

In FIG. 4, the feedback apparatus 10' as shown in FIG. 3 is operatively disposed between a forehead stop 16' and a lens 84 of a keratotometer 86. Keratotometers are well known in the art of eye examination and have an examining scope 88 defining a central optical axis. The split-ring =' is affixed to the lens 84 of the examining scope 88 by tightening the thumb screw 72 to clamp ring =' on the lens of the keratotometer. No particular orientation of the split-ring =' is required because generally the LED 70 aligns to the central optical axis no matter what the angular orientation of the split-ring =′.

As above, the examinee places his or her chin in the chin-cup 44′ and forehead against the forehead stop 16′. Pressure from the forehead against the forehead stop 16′ actuates the switch 48′, changing the condition of the switch 48′ to whichever state is used to indicate the condition that the patient's head is in place (i.e., with LED 70 on or off). Consequently, the examinee receives a perceptible feedback signal (in the form of the illuminated LED 70), representing the proper examination position. Should the examinee's forehead disengage the forehead stop 16′, the switch 48′ changes state to remind the examinee to move back into place. As in the dual LED embodiment discussed above, the arrangement of FIG. 4 has the advantage of providing an appropriate fixation point for the patient, thereby functioning cooperatively in the examining procedure and keeping the attention of the patient during the process.

Returning to FIG. 2, the alternative embodiment 10″ of an annunciator for the feedback apparatus comprising an audio speaker and oscillator circuit is shown by case 94, which contains an audio signal generating means responsive to the forehead switch or sensor. Case 94 has a socket 96 for plug-in connector 60 of the pigtail segment 62 for electrically interconnecting the audio speaker oscillator circuit 94 with the switch 48 and battery case 64. The oscillator can comprise any well-known tank circuit that is enabled by the switch or whose output is coupled to the speaker through the switch. The audio speaker (behind grill 98) is capable of emitting an audible tone via oscillating energy generated by the oscillator. Like the LEDs 52 and 70, the audio speaker and oscillator circuit 94 have an ON status and an OFF status for providing an appropriate indication, and can be used instead of or in addition to other annunciator devices.

A number of variations are possible within the scope of the invention. For example, different forms of sensors can be used to detect the positioning of the patient's head, such as spring biased switches, membrane switches (which are inherently resiliently biased), proximity sensors (e.g., capacitive or inductive), or devices that make or break an optical path between a source and a detector. Each type of sensor can be arranged to provide a switched output, for example via switched contacts or a switched solid state device such as a transistor or triac.

In the foregoing embodiments, the preferably-optical output device is mounted as an add-on to the viewing apparatus. Known viewing apparatus exist wherein a fixation light is already provided, typically such that a spot light source is visible to the patient when viewing down an optical axis. The invention is fully applicable to an embodiment wherein means are provided for switching such a pre-existing fixation signal on and off. In addition to electrical switching of the light source itself, as described, an electromechanical switching means is also possible, such as a pivotable half-silvered mirror or the like along the optical path, drivable by a solenoid to either insert or remove the optical image of the fixation light.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. An apparatus for physical examination of an examinee, the apparatus comprising:
   a support;
   a stop surface positioned to abut a portion of the examinee when the examinee is in a nominal examination position for the physical examination;
   a sensor associated with the stop surface, having means responsive to the examinee when in the examination position, the sensor detecting when the examinee is in and out of the examination position;
   switching means responsive to the sensor;
   a source of electrical power and an annunciator device, coupled in a circuit to be enabled and disabled by operation of the switching means, whereby operation of the annunciator device warns the examinee when the examinee is displaced from the examination position.

2. The apparatus according to claim 1, wherein the annunciator is chosen from the group consisting of a source of light, a source of sound and a tactile source.

3. The apparatus according to claim 1, wherein the annunciator comprises at least one light source mountable on a lens of a viewing device for an eye examination.

4. The apparatus according to claim 3, wherein the at least one light source is arranged as a fixation point to be focused upon by the examinee during the examination.

5. The apparatus according to claim 1, wherein the annunciator comprises two light sources mountable on opposite sides of a lens of a viewing device for an eye examination, whereby the examinee can fix on a selected one of the light sources for permitting illuminated viewing of the examinee's eye.

6. The apparatus according to claim 5, wherein the viewing device includes means for illuminating one of the examinee's eyes, whereby the examinee can fix on a selected one of the light sources to position the examinee's eyes via fixing another of the examinee's eyes on said one of the light sources.

7. The apparatus according to claim 4, wherein the annunciator comprises a source of a point of light disposed on the central optical axis of a keratotometer used in an eye examination.

8. The apparatus according to claim 1, wherein the stop surface comprises at least one of a forehead stop and a chin stop, abutting the examinee's head in the examination position.

9. The apparatus according to claim 8, wherein the sensor comprises an electrical switching means operable by detection of the examinee in the examination position, the switching means having an ON and an OFF condition coupled for one of enabling and disabling the annunciator.

10. The apparatus according to claim 9, wherein the switching means comprises a switch with contacts actuated by pressure from the examinee's forehead, the switch being resiliently biased to change state with presence and absence of said pressure.

11. The apparatus according to claim 1, wherein the support comprises a frame positioned in front of a lens of an eye examination instrument; and,
    the support comprises a forehead stop and a chin-cup mounted on the frame for positioning the examinee's head in a position to subject the examinee's eyes to the eye examination instrument.

12. An eye examination instrument, comprising:
   viewing means operable to view an eye of a patient;
   a head support for the patient, the head support defining an examination position at which the viewing means can view the eye;
   a sensor associated with the head support and operable to detect presence and absence of the patient at the examination position; and,
   an annunciator responsive to the sensor, the annunciator providing a signal perceptible to the patient for reminding the patient to maintain said examination position with the patient's head.

13. The instrument according to claim 12, wherein the annunciator comprises a light source arranged to define a fixation point for the patient during examination.

14. The instrument according to claim 12, wherein the annunciator comprises at least one light source disposed at an optical input to the instrument.

15. The instrument according to claim 14, wherein the light source is mounted via a bezel attachable to the instrument.

16. The instrument according to claim 12, wherein the sensor comprises a pressure sensitive switch responsive to pressure against the support.

17. The instrument according to claim 16, wherein the support comprises an abutment for a forehead of the patient and the sensor comprises a membrane switch mounted on the abutment.

18. The instrument according to claim 12, wherein the sensor is chosen from the group consisting of a spring biased switch, a membrane switches, a proximity sensor and means to make and break an optical path.

* * * * *

UNITED STATES PATENT AND TRADEMARK OFFICE
CERTIFICATE OF CORRECTION

PATENT NO. : 5,387,952
DATED : February 7, 1995
INVENTOR(S) : Harold Byer

It is certified that error appears in the above-indentified patent and that said Letters Patent is hereby corrected as shown below:

Column 6, lines 50, 51, 53, 54, 56, 59, 65, 67, 68, and column 7, line 2, change "=′" to read --50′--.

Signed and Sealed this

Twenty-fifth Day of April, 1995

*Attest:*

BRUCE LEHMAN

*Attesting Officer*     *Commissioner of Patents and Trademarks*